United States Patent
Goel

(10) Patent No.: US 7,345,190 B2
(45) Date of Patent: Mar. 18, 2008

(54) CARNITINE CONJUGATES AS DUAL PRODRUGS AND USES THEREOF

(75) Inventor: Om P. Goel, Ann Arbor, MI (US)

(73) Assignee: SSV Therapeutics, Inc., Ann Arbor, MI (US)

( * ) Notice: Subject to any disclaimer, the term of this patent is extended or adjusted under 35 U.S.C. 154(b) by 468 days.

(21) Appl. No.: 10/987,839

(22) Filed: Nov. 12, 2004

(65) Prior Publication Data

US 2005/0101572 A1 May 12, 2005

Related U.S. Application Data

(60) Provisional application No. 60/518,935, filed on Nov. 12, 2003.

(51) Int. Cl.
*C07C 69/00* (2006.01)

(52) U.S. Cl. ............ 560/129; 560/179; 560/147; 560/155

(58) Field of Classification Search ........ 560/129, 560/179, 147, 155
See application file for complete search history.

(56) References Cited

U.S. PATENT DOCUMENTS 4,963,525 A * 10/1990 Alexander et al. ............ 514/11
6,232,346 B1 * 5/2001 Sole et al. .................. 514/561

OTHER PUBLICATIONS

Alexander et al., 1987, CAS: 107:223274.*
Gaskell et al., 1986, CAS: 105:168289.*
Yamamoto et al., 1988, CAS: 109:51106.*
Yamaguchi et al., 1989, CAS: 111:75896.*
Huang et al., 1992, CAS: 116:18011.*
Pourfarzam et al., 1993, CAS: 119:91967.*
Nakanishi et al., 1994, CAS: 120:245706.*
Montgomery et al., 1989, CAS: 110:169579.*
Millington et al., 1989, CAS: 111:190899.*

* cited by examiner

*Primary Examiner*—Rei-tsang Shiao
(74) *Attorney, Agent, or Firm*—Technology Law, PLLC; Karen L. Kimble

(57) ABSTRACT

The present invention discloses novel dual prodrug compositions of Formula 1,

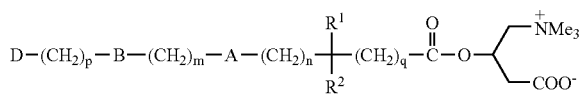

Formula 1 wherein A is a single bond, —O—, or —$CH_2$—; m and n vary from 0 to 15; p and q vary from 0 to 4; B is a single bond or —$CR^3R^4$; D is selected from the group consisting —$CO_2R^5$, —$OR^6$, —$OCOR^7$, —$SO_3R^8$, —$SO_2NH_2$, —$OPO(OR^9)(OR^{10})$, —$OPO(OR^9)(NH_2)$, —$OPO(OR^9)$—O—$PO(OR^{10})(OR^{11})$,

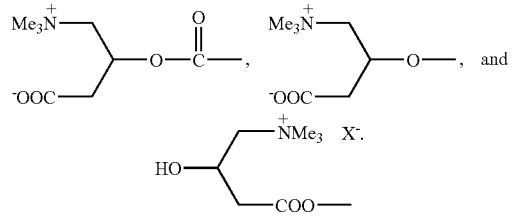

$R^1$ to $R^{11}$ are various substituents selected to optimize the physicochemical and biological properties such as, lipophilicity, toxicity, bioavailability, and pharmacokinetics of compounds of Formula 1. These compounds are useful for the treatment of various cardiovascular and neurological disorders.

4 Claims, No Drawings

CARNITINE CONJUGATES AS DUAL PRODRUGS AND USES THEREOF

This application claims benefit of priority of Provisional Application No. 60/518935, filed on Nov. 12, 2003.

FIELD OF THE INVENTION

This present invention relates to novel carnitine ester and ether conjugates of hypolipidemic agents and pharmaceutically acceptable salts thereof. The novel compositions of the present invention are useful for the treatment of cardiovascular diseases, metabolic diseases, obesity, diabetes, gastrointestinal disorders, inflammation, cancer, anemia, renal anemia, Alzheimer's diseasse; and for modulating peroxisome proliferation by peroxisome proliferator-activated receptors (PPARs).

BACKGROUND OF THE INVENTION

It is to be noted that throughout this application various publications are referenced by Arabic numerals within brackets. Full citations for these publications are listed at the end of the specification. The disclosures of these publications are hereby incorporated by reference in their entireties in order to more fully describe the state of the art to which this invention pertains.

Coronary heart-disease (CHD) is a leading cause of troublesome quality of life, and mortality among the populations of the developed nations and the economically fast-growing countries with worldwide reise in obesity, diabetes, including among young adults, due to high-calories diets and poor exercise time. The cardiovascular disease is characterized by clogged arteries and reduced supply of blood and nutrients to the heart muscle caused by lipid deposition inside the arterial wall. Hyperlipidemia or hyperlipoproteinemia (form lipid-protein complexes) may be caused by genetic factors or by obesity and metabolic disorders. Lipid-protein complexes are spherical aggregates consisting of a hydrophobic core composed of lipids (triglycerides and cholesterol esters) surrounded by hydrophilic exterior shell of about 2 nm composed of apoproteins, cholesterol, and phospholipids. The hydrophilic polar surface keeps the lipids dissolved and circulating in the plasma. Based on the size and density, four main lipoproteins prevalent in the plasma: chylomicrons, very low density lipoprotein (VLDL), low density lipoprotein (LDL or LDL-C), and high density lipoprotein (HDL oar HDL-C). Chylomicrons and VLDL are rich in triglycerides and cholesterol. The are the sources of fatty acids in muscles and adipose tissues. LDL-C particles are rich in cholesterol and are produced in the liver from dietary cholesterol, from liver-synthesized cholesterol, and from remnants of chylomicrons and VLDL that have entered the extrahepatic tissues from the general circulation [1].

High levels of LDL-C (referred to as 'bad cholesterol') is a well established major risk factor in CHD, but is effectively treated with HMG-CoA reductase inhibitors (statins) leading to substantial reduction in cardiovascular morbidity and mortality [2]. HDL-C particles (referred to as 'good cholesterol') are responsible for a cleansing mechanism called 'reverse cholesterol transport,' where the cholesterol is transported from extrahepatic tissues to the liver for catabolic destruction and excretion. It is widely accepted that low levels of HDL-C and high levels of triglycerides in plasma are important risk factors contributing to CHD [3].

Levocarnitine (L-carnitine or vitamin $B_T$) belongs to a class of water soluble vitamins which includes vitamin B-12, folic acid, biotin, vitamin B-6, and mevalonic acid. It occurs naturally, and serves as a cofactor in fatty acid metabolism for energy production. This cofactor functions by birding activated fatty acids in the form of acyl carnitine (carnitine shuttle). Use of 1-carnitine in the treatment of hyperlipoproteinemia, hyperlipidemia, and myocardial dysfunction has been the subject of intensive investigation [4-9]. L-carnitine has also been reported to be useful as an adjuvant therapy in the management of renal anemia [10]. Propionyl carnitine (the propionic ester of carnitine) has been shown to improve cardiac function [11, 12]. Acetyl carnitine has been proposed as a possible therapeutic agent for Alzheimer's disease [13]. Recently, CPS 124,a carnitine monothiophosphate derivative which is a reversible and competitive inhibitor of carnitine palmitoyl transferase I, is reportedly undergoing clinical development for the treatment of non-insulin dependent diabetes mellitus (NIDDM) [14].

In humans, fibrates such as clofibrate, bezafibrate, fenofibrate, etofibrate, gernfibrozil, G10-2331, which are agonists of PPAR-alpha have been successfully used to treat hypertriglyceridemia. They function by increasing the clearance and decreasing the synthesis of VLDL. The fibtrates, however, have only a modest effect (10-20%) in increasing HDL-C levels [15, 16]. Clinical development of cardioprotective HDL-C elevating agents is a major current therapeutic goal. Recently, it was shown that oxa substituted $\alpha,\omega$-alkanedicarboxylic acids and related compounds raise serum HDL-levels significantly [17]. In particular, CI-1027 has been in clinical trials. Also, long chain $\alpha,\omega$-alkanedicarboxylic acids are also in clinical development as hypolipidemic agents [18,19].

In view of the extensive work in the treatment of hyperlipoproteinemia, hyperlipidemia, and myocardial dysfunction with L-camnitine, L-propionyl carnitine, CI-1027 and its analogs, and fibric acids, it is surprising that covalent conjugates of any two or more of these drugs have not been proposed. Therefore, the present invention introduces a novel concept referred to as 'double prodrug' approach which involves the preparation of novel covalent conjugates comprising two or more drugs, and their use in the treatment of various cardiovascular disorders. A suitable covalent attachment of two more of these cardiovascular agents will have a significant therapeutic value in that a single molecular entity may have multiple therapeutic effects resulting from diverse, but synergistic mechanism of action, and controlled release of both drugs in vivo through enzymatic hydrolysis of the conjugate. The concept of the present invention is not limited to cardiovascular applications; other therapeutic applications, including CNS disorders, diabetes, cancer, inflammation, and the like are also contemplated.

SUMMARY OF THE INVENTION

The present invention discloses novel dual prodrug compositions of Formula 1,

Formula 1

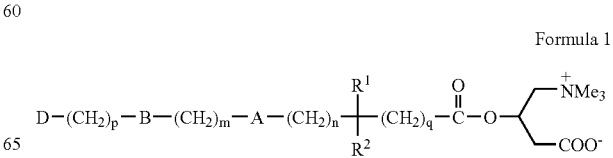

wherein A is a single bond, —O— or —CH$_2$—; m and n vary from 3 to 15; p and q vary from 0 to 4; B is a single bond or —CR$^3$R$^4$; D is selected from the group consisting of —CO$_2$R$^5$, —OR$^6$, —OCOR$^7$, —SO$_3$R$^8$, —SO$_2$NH$_2$, —OPO(OR$^9$)(OR$^{10}$), —OPO(OR$^9$)(NH$_2$), —OPO(OR$^9$)—O—PO(OR$^{10}$)(OR$^{11}$),

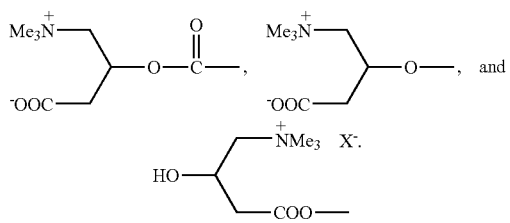

R$^1$ to R$^{11}$ are various substituents selected to optimize the physicochemical and biological properties such as, lipophilicity, toxicity, bioavailability, and pharmacokinetics of compounds of Formula 1. These include, but are not limited to hydrogen, alkyl, alkenyl, alkynyl, cyloalkyl, acyl, hydroxyl, hydroxyalkyl, aryl, amino, aminoalkyl, alkoxyl, aryloxyl, carboxyl, halogen, alkoxycarbonyl, trihaloalkyl, cyano, and other suitable electron donating or electron withdrawing groups.

DETAILED DESCRIPTION OF THE INVENTION

The present invention provides novel dual prodrug compounds and the corresponding pharmaceutically acceptable salts thereof of Formula 1, Formula 1

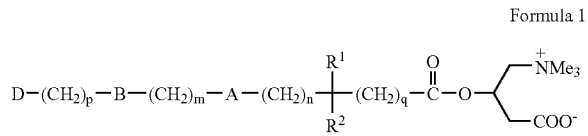

wherein A is a single bond, —O— or —CH$_2$—; m and n vary from 0 to 15;p and q vary from 0 to 4; B is a single bond or —CR$^3$R$^4$; D is selected from the group consisting of —CO$_2$R$^5$, —OR$^6$, —OCOR$^7$, —SO$_3$R$^8$, —SO$_2$NH$_2$, —OPO(OR$^9$)(OR$^{10}$), —OPO(OR$^9$)(NH$_2$), —OPO(OR$^9$)—O—PO(OR$^{10}$)(OR$^{11}$),

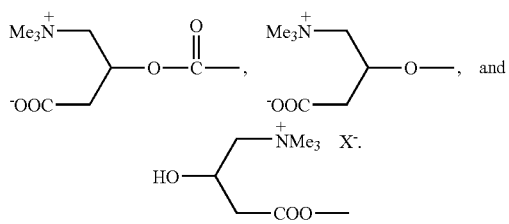

R$^1$ to R$^{11}$ are independently selected from the group consisting of hydrogen; C$_1$-C$_6$ alkyl; C$_3$-C$_6$ cycloalkyl; C$_2$-C$_6$ alkenyl; C$_6$ alkynyl; C$_5$-C$_{10}$ aryl unsubstituted or substituted with C$_1$-C$_6$ alkyl, hydroxyl, C$_1$-C$_6$ alkoxyl, 1,3-dioxolanyl, cyano, halo, nitro, trihaloalkyl, carboxyl, C$_1$-C$_6$ acyl, C$_1$-C$_6$ hydroxyalkyl, anrino, C$_1$-C$_6$ alkylamino, C$_1$-C$_6$ dialkylamino, C$_1$-C$_6$ acylamino, mercapto, C$_1$-C$_6$ alkylthio, C$_1$-C$_6$ mercaptoalkyl, and C$_1$-C$_6$ alkxoylcarbonyl; and C$_5$-C$_6$ arylalkyl unsubstituted or substituted with C$_1$-C$_6$ alkyl, hydroxyl, C$_1$-C$_6$ alkoxyl, 1,3-dioxolanyl, cyano, halo, trihaloalkyl, carboxyl, C$_1$-C$_6$ acyl, C$_1$-C$_6$ hydroxyalkyl, amino, C$_1$-C$_6$ alkylamino, C$_1$-C$_6$ dialkylamino, mercapto, C$_1$-C$_6$ alkylthio, C$_1$-C$_6$ mercaptoalkyl, and C$_1$-C$_6$ alkxoylcarbonyl; C$_1$-C$_6$ carboxyalkyl; C$_1$-C$_6$ acylamino; C$_1$-C$_6$ sulfonatoalkyl; C$_1$-C$_6$ sulfamylalkyl; and C$_1$-C$_6$ phosphonatoalkyl. R$^1$ and R$^2$ or R$^3$ and R$^4$ may optionally be tethered together to form 3- to 7-membered alicyclic ring.

A preferred embodiment of the present invention is represented by Formula 1,wherein wherein A is —O— or —CH$_2$—; m and n vary from 0 to 6;p and q vary from 0 to 3; B is —CR$^3$R$^4$; D is selected from the group consisting of —CO$_2$R$^5$, —OR$^6$, and

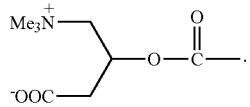

R$^1$ to R$^6$ are independently selected from the group consisting of hydrogen; C$_1$-C$_6$alkyl, and C$_3$-C$_6$ cycloalkyl. R$^1$ and R$^2$ or R$^3$ and R$^4$ may optionally be tethered together to form 3- to 7-membered alicyclic ring.

Another preferred embodiment of the present invention is represented by Formula 1, wherein A is —O— or —CH$_2$—; m and n vary from 0 to 6;p and q vary from 0 to 3; B is —CR$^3$R$^4$; D is selected from the group consisting of —CO$_2$R$^5$, —OR$^6$, and

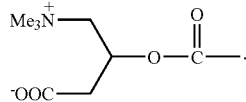

R$^1$ to R$^6$ are independently hydrogen or C$_1$-C$_6$ alkyl.

Another preferred embodiment of the present invention is represented by Formula 1, wherein A —O— or CH$_2$—; m is 4;n is 4;p varies from 0 to 3;q is 0 or 1; B is —CR$^3$R$^4$; D is selected from the group consisting of —CO$_2$R$^5$, —CH$_2$OR$^6$, and

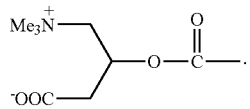

R$^1$ to R$^4$ are methyl groups. R$^5$ is hydrogen or an ethyl group. R$^6$ is hydrogen.

Another preferred embodiment of the present invention is represented by Formula 1, wherein A is a single bond m is 0 or 1;n is 0 or 1;p is 0 or 1;q is 0; B is a single bond; D are —OR$^6$; R$^3$ and R$^4$ are methyl groups.

The compounds belonging to Formula 1 can be synthesized according to the method known in the art. The dual prodrug of the present invention can be prepared by standard methods well known in the art. Alkylation of α,ω-dihaloalkane 3 with 2 equivalents of the anion 3 (prepared by deprotonation of ethyl isobutyrate with lithium diisopropy-lamimde, LDA) gives the key intermediate, the diester 4 (Scheme 1) from which many of the prodrugs

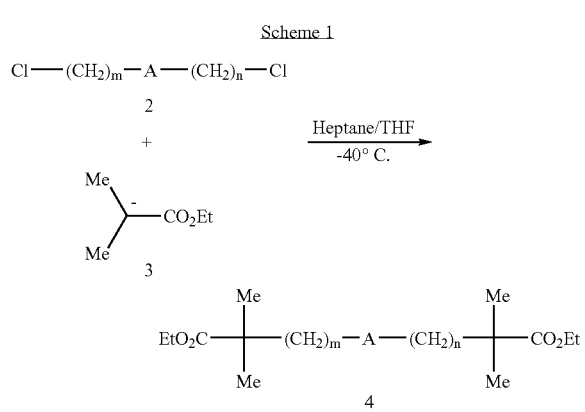

of the present invention can be prepared. The camitine prodrugs 6-8 can be prepared from the diester 4 as shown in Scheme 2. The monoacid 5, prepared by careful saponification of

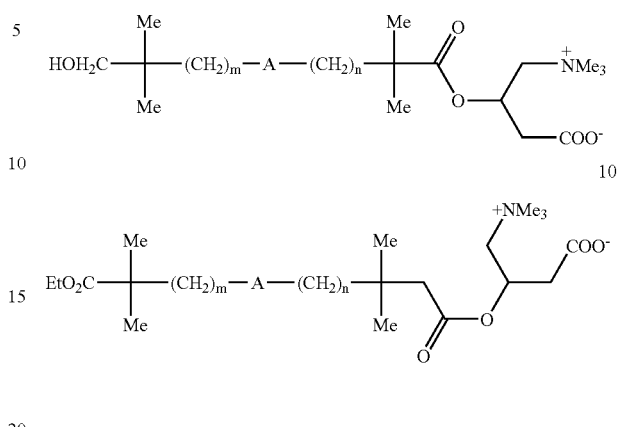

method and transformed to the chain elongated to the dual prodrug 10. Similarly, the diester 4 can be hydrolyzed to the diacid, homologated at both ends of the chain by Arndt-Eistert method, and condensed with carnitine to give the dual prodrugs 11 and 12. Two-carbon

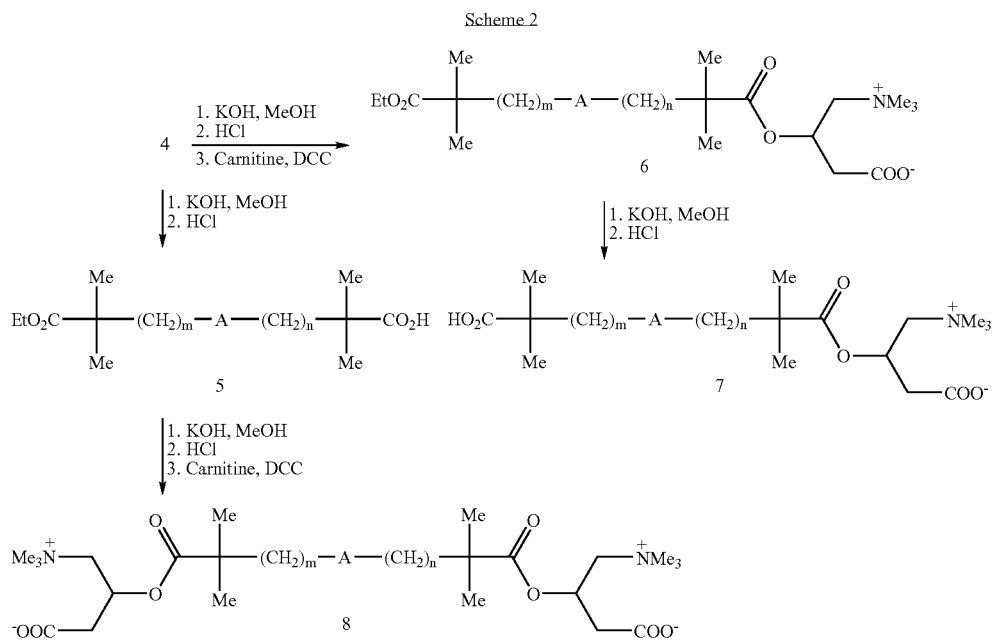

the diester 4, is condensed with carnitine using dicyclohexylcarbodiimide (DCC) in DMF, THF, or DMSO, or water soluble carbodiimides such as ethyl-N-(3-dimethylamino)propyl-carbodiimide (EDC). The monoacid 5 can be reduced with borane-THF to the corresponding alcohol ester, which then can be transformed to the dual prodrug 9 by the methods outlined in Scheme 1 The acid 5 can also be homologated using the Arndt-Eistert

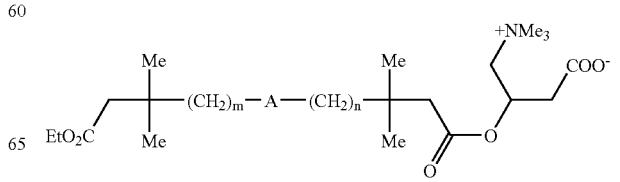

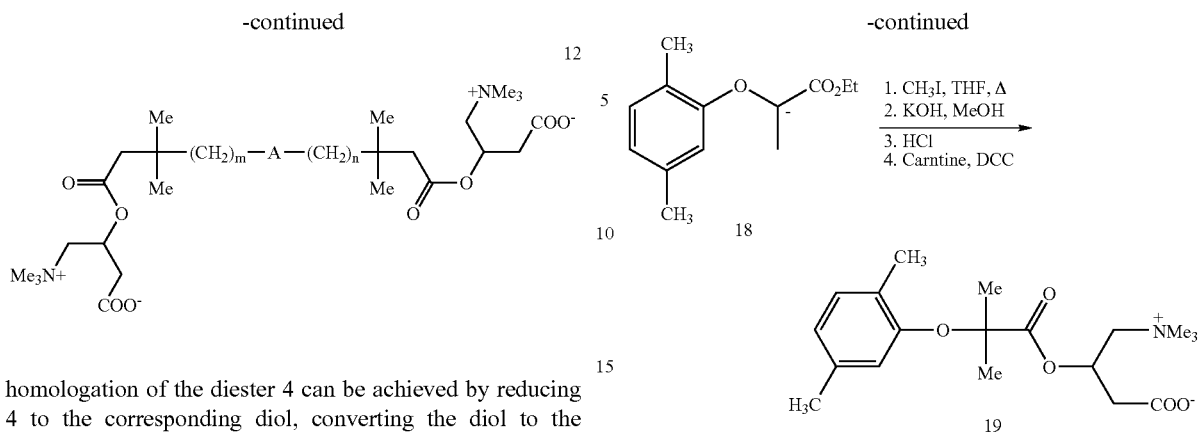

homologation of the diester 4 can be achieved by reducing 4 to the corresponding diol, converting the diol to the dihalide, alkylating the dihalide with diethyl malonate, and hydrolyzing the tetraester to the homologated diester 13, which can then be transformed to the carnitine dual prodrug derivatives as described in Scheme 1.

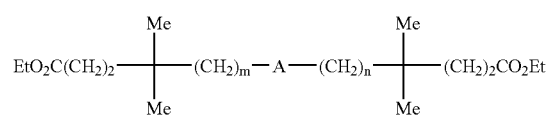

The carnitine-fibrate dual prodrugs can also be prepared by analogous methods outlined in previous schemes. The gemfibrozil conjugate 17 can be prepared as outlined in Scheme 3. The starting material 15 can be prepared by the alkylation of ethyl isobutyrate

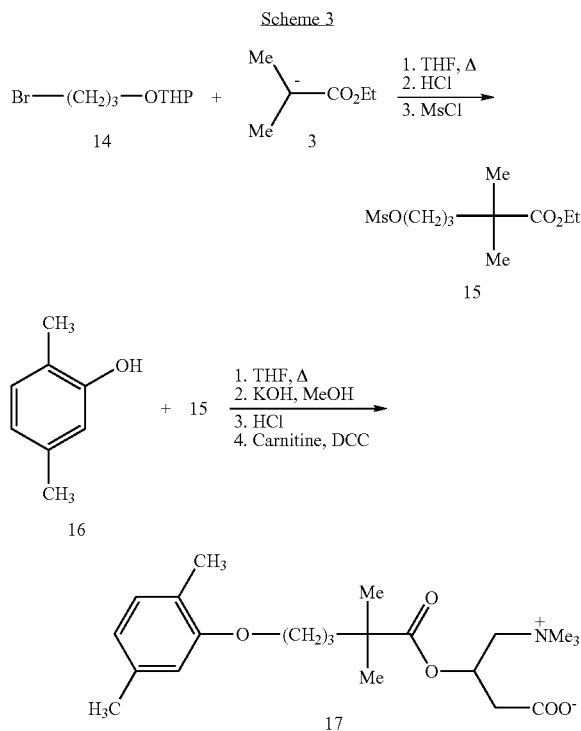

with THP-protected 3-bromopropanol. The anion 18 can be prepared by alkylating the phenol 16 with ethyl 2-bromopropionate followed by deprotonation with lithium diisopropylamide.

Compounds of the present invention may exist as as a single stereoisomer or as mixture of enantiomers and diastereomers whenever chiral centers are present. Individual stereoisomers can be isolated by the methods well known in the art: diastereomers can be separated by standard purification methods such as fractional crystallization or chromatography, and enantiomers can be separated either by resolution or by chromatography using chiral columns.

The pharmaceutical composition may also contain physiologically tolerable diluents, carriers, adjuvants, and the like. The phrase "pharmaceutically acceptable" means those formulations which are, within the scope of sound medical judgment, suitable for use in contact with the tissues of humans and animals without undue toxicity, irritation, allergic response and the like, and are commensurate with a reasonable benefit/risk ratio. Pharmaceutically acceptable salts are well-known in the art, and are described by Berge et al. [20], incorporated herein by reference. Representative salts include, but are not limited to acetate, adipate, alginate, citrate, aspartate, benzoate, benzenesulfonate, chloride, bromide, bisulfate, butyrate, camphorate, camphor sulfonate, gluconate, glycerophosphate, hemisulfate, heptanoate, hexanoate, fumarate, maleate, succinate, oxalate, citrate, hydrochloride, hydrobromide, hydroiodide, lactate, maleate, nicotinate, 2-hydroxyethansulfonate (isothionate), methane sulfonate, 2-naphthalene sulfonate, oxalate, palmitoate, pectinate, persulfate, 3-phenylpropionate, picrate, pivalate, propionate, tartrate, phosphate, glutamate, bicarbonate, p-toluenesulfonate, undecanoate, lithium, sodium, potassium, calcium, magnesium, aluminum, ammonium, tetramethyl ammonium, tetraethylammonium, methylammonium, dimethylammonium, trimethylammonium, triethylammonium, diethylammonium, and ethylammonium, and the like.

The pharmaceutical compositions of this invention can be administered to humans and other mammals enterally or parenterally in a solid, liquid, or vapor form. Enteral route includes, oral, rectal, toipical, buccal, and vaginal administration. Parenteral route intravenous, intramuscular, intraperitoneal, intrasternal, and subcutaneous injection or infusion. The compositions can also be delivered through a catheter for local delivery at a target site, via an intracoronary stent (a tubular device composed of a fine wire mesh), or via a biodegradable polymer.

The active compound is mixed under sterile conditions with a pharmaceutically acceptable carrier along with any needed preservatives, excipients, buffers, or propellants. Opthalmic formulations, eye ointments, powders and solutions are also contemplated as being within the scope of this invention. Actual dosage levels of the active ingredients in the pharmaceutical formulation can be varied so as to achieve the desired therapeutic response for a particular patient. The selected dosage level will depend upon the activity of the particular compound, the route of administration, the severity of the condition being treated, and prior medical history of the patient being treated. However, it is within the skill of the art to start doses of the compound at levels lower than required to achieve the desired therapeutic effect and to increase it gradually until optimal therapeutic effect is achieved. The total daily dose of the compounds of this invention administered to a human or lower animal may range from about 0.0001 to about 1000 mg/kg/day. For purposes of oral administration, more preferable doses can be in the range from about 0.001 to about 5 mg/kg/day. If desired, the effective daily dose can be divided into multiple doses for purposes of administration; consequently, single dose compositions may contain such amounts or submultiples thereof to make up the daily dose.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated, the severity of the disorder; activity of the specific compound employed; the specific composition employed, age, body weight, general health, sex, diet of the patient; the time of administration, route of administration, and rate of excretion of the specific compound employed, and the duration of the treatment. The compounds of the present invention may also be administered in combination with other drugs if medically necessary.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Dosage forms for topical administration include powders, sprays, ointments and inhalants. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

The present invention also provides pharmaceutical compositions that comprise compounds of the present invention formulated together with one or more non-toxic pharmaceutically acceptable carriers. Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art [21], incorporated herein by reference.

The Examples which follow are presented to describe preferred embodiments and utilities of the invention and are not meant to limit the invention unless otherwise stated in the claims appended hereto. The description is intended as a non-limiting illustration, since many variations will become apparent to those skilled in the art in view thereof. It is intended that all such variation within the scope and spirit of the appended claims be embraced thereby. Changes can be made in the composition, operation, and arrangement of the method of the present invention described herein without departing from the concept and scope of the invention as defined in the claims.

EXAMPLE 1

Preparation of Ester Dual Prodrug 6 Wherein $m=n=4$, and $p=q=0$

Step 1. A solution of 12.8 g (0.1 1 mole) of ethyl isobutyrate in 130 mL of dry THF is cooled to $-30°$ C., and a 2M solution (0.105 mole) of lithium diisopropylamide in heptane is added slowly keeping the temperature at $-30°$ C. After stirring at this temperature for 30 minutes, a solution of 9.95 g (0.05 mole) of bis-(4-chlorobutyl)ether in 100 mL of dry THF is added. The suspension is stirred and allowed to warm to room temperature. It is cooled to 5 deg. C., and quenched with slow addition of 50 mL of water with vigorous stirring. The organic layer is separated, and the aqueous layer extracted with toluene or heptane. The combined organic layers are dried (optional), over anhydrous $MgSO_4$, and then evaporated to give a white solid, which is purified by recrystallization from toluene/heptane or THF/heptane to give the diester 4, wherein $m=n=4$, and $p=q=0$.

Step 2: The diester from Step 1 (12.11 g, 0.05 mole) is dissolved in 100 mL of absolute ethanol and a solution of 0.5 mole of KOH in 50 mL of absolute ethanol is added. After stirring for 18 hours, the solvent is removed, and the residue acidified with cold 6N HCl to pH 1. The precipitate is collected and washed thoroughly with water and heptane, and dried to give a white solid. It is further purified by recrystallization from aqueous ethanol to give 8-9 g of mono acid mono ester 5, wherein $m=n=4$, and $p=q=0$. The monoacid monoester can be then condensed with dl- or l-carnitine as described below.

Alternatively, the crude mono acid potassium salt after saponification, is stirred in toluene, and all residual ethanol is removed by azeotropic distillation. The remaining dry solid is suspended in dry DMF and stirred with an equivalent of oxalyl chloride. The precipitated KCl is filtered off and the filtrate, the monoester-monoacid chloride wherein $m=n=4$, and $p=q=0$, is used as such in the coupling reaction with dl- or l-carnitine as described below.

Step 3: The monoacid ethyl ester (5.35 g, 0.025 mole) from Step 2 is dissolved in 75 mL of dry THF. Then 1-hydroxybenzotriazole is added (0.34 g, 0.0025 mole) followed by dry L-carnitine or DL-carnitine (4.43 g, 0.0275 mole) dissolved in 20 mmL of DMF is added. The solution is cooled to $0°$ C., and a 1 M solution of dicyclohexylcarbodiimide in $CH_2Cl_2$ (0.025 mole) is slowly added with stirring, The precipitated dicyclohexyl urea is filtered off, and the filtrate is acidified to pH 8. The precipitated product 6 is collected as an internal salt, which is recrystallized from aqueous ethanol to give a pure product. Alternatively, the pH above may be adjusted to 0-1 with 6N HCL while keeping cold. The final prodrug product 6, is then obtained as a hydrochloride salt.

Alternatively, the acid chloride Step 2 above is dissolved in 50 mL of THF or benzene, and 10% v/v of DMF. The solution is treated with an equivalent amount of L-carnitine or DL-carnitine, followed by an equivalent amount of triethylamine or diisopropylethyl amine and a catalytic amount of DMAP. When the reaction is complete, the solid is collected, dissolved in water, and the product isolated as describe in the previous paragraph.

EXAMPLE 2

Preparation of Acid Dual Prodrug 7, Wherein $m=n=4$, and $p=q=0$

The ester prodrug 6, obtained in Example 1, is dissolved in 1 equivalent of aqueous sodium hydroxide at 0-5° C. When all the ethyl ester has hydrolyzed (indicated by nmr of a $CHCl_3$ extract), the pH is adjusted to 4-5 to precipitate the acid prodrug 7, which is collected and recrystallized from aqueous methanol.

EXAMPLE 3

Preparation of Bis(Carnitine) Dual Prodrug 8, Wherein $m=n=4$, and $p=q=0$

The acid prodrug 7 from Example 2 (0.025 mole) is dissolved in 75 mL of dry THF. Then 1-hydroxybenzotriazole is added (0.0025 mole) followed by dry L-carnitine or DL-carnitine (0.0275 mole) dissolved in 20 mL of DMF is added. The solution is cooled to $0°$ C., and a 1M solution of dicyclohexylcarbodiimide in $CH_2Cl_2$ (0.025 mole) is slowly added with stirring. The precipitated dicyclohexyl urea is filtered off, and the filtrate is acidified to pH 8. The precipitated product 8 is collected as an internal salt, which is recrystallized from aqueous ethanol or any other suitable solvent.

EXAMPLE 4

Conversion of the Acid Prodrug 7 into the Corresponding Alcohol Prodrug, Wherein m=n=4,and p=q=0,and B is —$CH_2OH$ The acid prodrug 7 is dissolved in THF/10% DMF, and an equivalent of pivaloyl chloride is added at 0-5° C. followed by an equivalent of triethyl amine. The triethylamine hydrochloride is filtered off and the filtrate of mixed anhydride is reacted with an excess of sodium borohydride solution in THF. The reaction mixture is quenched with acetic acid, and the solution diluted with heptane to precipitate the product. The product is collected and purified by recrystallization from aqueous methanol or any other suitable solvent.

EXAMPLE 5

Preparation of Ester Prodrug 11, Wherein m=n=4 and p=q=1

Step 1. A one molar solution of Grignard reagent $BrMg(CH_2)_4$—O—$(CH_2)_4MgBr$ in diethyl ether is prepared from Bis(4-bromobutyl)ether, and magnesium turnings in the usual manner under an inert atmosphere. To this solution is slowly added a solution of 400.46 g (2 moles) of diethyl isopropylidinemalonate dissolved in 2 liter of dry diethylether. The reaction mixture is refluxed 12 hours and the mixture treated with aqueous ammonium chloride. The ether solution is separated from the salts, and concentrated to dryness. The residue is purified by distillation using a wiped-film evaporator to give the intermediate tetraethylester, $(EtOOC)_2CHC(CH_3)_2(CH_2)_4$—O—$(CH_2)_4C(CH_3)_2CH(COOEt)_2$.

Step 2. The purified tetraethyl ester from Step 1 above is dissolved in absolute ethanol, and treated with 2.1 equivalents of KOH in absolute ethanol. The mixture is stirred at 25-40° C. till the pH is about 9. The solvent is removed under vacuum and the residue heated in an oil bath at 200° C. until gas evolution has ceased. The residue is recrystallized to give the pure diester $EtOOCCH_2C(CH_3)_2(CH_2)_4$—O—$(CH_2)_4C(CH_3)_2CH_2COOEt$.

Step 3. The compound Step 2 above is dissolved in absolute ethanol, and treated with 1 equivalent or 5% molar excess of KOH in absolute ethanol. Whenthe hydrolysis is complete, the solvent is removed in vacuum, the residue dissolved in cold water, and the pH adjusted to 1,to precipitate a white solid of mono acid mono ester, which is collected and purified by recrystallization to give pure $EtOOCCH_2C(CH_3)_2(CH_2)_4$—O—$(CH_2)_4C(CH_3)_2CH_2COOH$.

Step 4. The final ester prodrug 11 is prepared by the same procedure as described in Example 1, Step 3.

EXAMPLE 6

Preparation of the Ester Dual Prodrug 10, Wherein m=n=4 p=0,and g =1

Step 1. A solution of t-butyl isobutyrate (0.11 mole) in 130 mL of dry THF is cooled to −30° C., and a 2M solution (0.105 mole) of lithium diisopropylamide in heptane is added slowly keeping the temperature at −30° C. After stirring at this temperature for 30 minutes, a solution of 1,4-dibromobutane (0.05 mole) in 100 mL of dry THF is added. The suspension is stirred and allowed to warm to room temperature. It is cooled to 5° C., and quenched with slow addition of 50 mL of water with vigorous stirring. The organic layer is separated, and the aqueous layer extracted with toluene or heptane. The combined organic layers are dried (optional), over anhydrous $MgSO_4$, and then evaporated to give a white solid, which is purified by recrystallization from toluene/heptane or THF/heptane to give the bromoester, t-$BuOOCC(CH_3)_2(CH_2)_4Br$.

Step 2. A one molar solution of Grignard reagent THP—$O(CH_2)_4$—O—$(CH_2)_4MgBr$ in diethyl ether is prepared from THP—$O(CH_2)_4$—O—$(CH_2)_4Br$ and magnesium turnings in the usual manner under an inert atmosphere. To this solution is slowly added a solution of 1 mole of diethyl isopropylidinemalonate dissolved in 2 liter of dry diethylether. The reaction mixture is refluxed 12 hours and the mixture treated with aqueous ammonium chloride. The ether solution is separated from the salts, and concentrated to dryness. The residue is purified by distillation using a wiped-film evaporator to give the diethylester, THP—O$(CH_2)_4C(CH_3)_2CH(COOEt)_2$. The tetrahydropyranyl group is then removed by treating the above THP ether with IN HCl in THF followed by usual workup to give the corresponding alcohol HO$(CH_2)_4C(CH_3)_2CH(COOEt)_2$.

Step 3. The diester from Step 2 above is dissolved in absolute ethanol and treated with 1.1 equivalents of KOH in absolute ethanol. The mixture is stirred at 25-40° C. till the pH is about 9. The solvent is removed under vacuum and the residue heated in an oil bath at 200° C. until gas evolution has ceased. The residue is recrystallized to give the pure monoester HO$(CH_2)_4C(CH_3)_2CH_2COOEt$.

Step 4. A solution of the alcohol from Step 3 (0.010 mol) in dry THF (20 mL) is cooled to 0° C. and carefully treated with 1.2 equivalents of sodium hydride (60% suspension in oil) in an inert atmosphere. After stirring at this temperature for 30 minutes, a solution of the bromide from Step 1 (0.011 mol) in THF (20 mL) is added dropwise. After the addition is complete, the entire mixture is heated under reflux for 24 hours. After cooling, the reaction mixture is poured onto water and extracted with methylene chloride. The organic layer is separated, washed with water, dried over $MgSO_4$, filtered, and the filtrate taken to dryness. The crude product is then treated with 50% trifluoroacetic acid in methylene chloride and kept at ambient temperature for 1 hour. Thereafter, the reaction mixture is poured onto water and extracted with methylene chloride. The organic layer is separated, washed with water, dried over $Na_2SO4$,filtered, and the filtrate taken to dryness. The crude monoacid, HOOCC$(CH_3)_2(CH_2)_4$—O—$(CH_2)_4C(CH_3)_2CH_2COOEt$ is purified by recrystallization or chromatography.

Step 5. The final ester prodrug 10 is prepared by the same procedure as described in Example 1, Step 3.

EXAMPLE 7

Preparation of the Ester Dual Prodrug 17 Wherein A and D are Single Bonds, m=n=q=0,and 4,p=3.and B is —$OR^6$ Step 1. Alkylation of 3-bromopropanol THP ether (10 mmol) with ethyl isobutyryl anion is carried out in the same manner as described in Step 1, Example 1. The alkylated product is then dissolved in THF (20 mL) and treated with 2M HCl (10 mL) and stirred at ambient temperature for 4 hours. The solvent and excess HCl is removed by evaporation in vacuo and the residue is purified by high vacuum distillation to give pure ethyl 5-hydroxy-2-dimethylpentanoate.

Step 2. A solution of the alcohol from Step 1 (10 mmol) and triethylamine (15 mmol) in dry THF (20 mL) is cooled to 0° C. and carefully treated with methanesulfonyl chloride (11 mmol) and stirred at ambient temperature for 4 hours. The reaction mixture is poured onto water and extracted with methylene chloride. The organic layer is separated, washed with water, dried over MgSO$_4$, filtered, and the filtrate taken to dryness. The crude material is used as such in the next step.

Step 3. A mixture of the mesylate from Step 2 (10 mmol) and 2,5-dimethylphenol (10 mmol), and finely-ground anhydrous potassium carbonate (15 mmol) in glyme (20 mL) is heated under reflux for 8 hours. The reaction mixture is filtered hot and the filtrate evaporated in vacuo. The residue is purified by chromatography or recrystallization to give the ethyl ester.

Steps 4 and 5. The ethyl ester is then saponified according to the procedure described in Step 2 and condensed with carnitine according to the procedure described in Step 3, Example 1 to give the desired dual prodrug 17.

EXAMPLE 8

Preparation of the Ester Dual Prodrug 17, Wherein A and D are Single Bonds m=n=p=q=0; and B is OR$^6$ Step 1. A solution of ethyl 2-methyl-3-(2,5-dimethyl) phenoxyacetate (0.11 mole) in 130 mL of dry THF is cooled to −30° C., and a 2M solution (0.105 mole) of lithium Diisopropylamide in heptane is added slowly keeping the temperature at −30° C. After stirring at this temperature for 30 minutes, a solution of methyl iodide (0.05 mole) in 100 mL of dry THF is added. The suspension is stirred and allowed to warm to room temperature. It is cooled to 5° C., and quenched with slow addition of 50 mL of water with vigorous stirring. The organic layer is separated, and the aqueous layer is extracted with toluene or heptane. The combined organic layers are dried (optional), over anhydrous MgSO4,and then evaporated to give a white solid, which is purified by recrystallization from toluene/heptane or THF/heptane to give the ethyl 2,2-dimethyl-3-(2,5-dimethyl)-phenoxyacetate.

Step 2-4. The conversion of the ester from Step 1 to the final compound 19 is carried out in the same manner as described in Steps 3-5, Example 7.

References

1. A. Ziegler, K. Mohr, and E. Bieger. *Color Atlas of Pharmacology, 2$^{nd}$ Edition*,pp. 154-157. Thieme Publishers, 2000.
2. Scandinavian Simvastatin Study Group. *Lancet* 1994, 344, 1383.
3. NCEP Panel. *Circulation* 1994, 89, 1329.
4. C. Carazza. U. S. Pat. No. 4,255,449, 1981.
5. M. Ramacci. U. S. Pat. No. 4,315,944, 1982.
6. N. Silliprandi. *Hypolipidemic Drugs*. G. Ricci (Ed.). New York: Ravan, 1982.
7. N. Yamazaki. *Lipid* 1990, 1(2).
8. De Pauly et al. *American Journal of Kidney Diseases* 2003, 41(4).
9. M. Calvari et al. *Basic Research in Cardiology* 2000, 95(2), 75.
10. B. Cianciaruso et al. *Nephrology* 2002, 137, 426.
11. L. R. Wiseman, R. N. Brogden. *Drugs and Aging* 1998.
12. R. Ferrari, I Anand. *Developments in Cardiovascular Medicine* 1995, 162, 323.
13. J. W. Pettegraw, R. J. McClure. *Expert Review of Neurotherapeutics* 2002, 2(5), 647.
14. R. C. Anderson. *Curr. Pharm. Des.* 1998,4, 1-15.
15. B. Stales, J. Dallongville, J. Anwerx, K. Shoonjans, E. Lieterdorf, J. C. Furchart. *Circulation* 1998, 98, 2088.
16. H. J. Harwood, E. S. Hamanaka. *Emerging Drug* 1998, 3, 147.
17. C. L. Bisgaier, P. L. Creager, A. R. Saltiel, S. R. Tafuiri. U. S. Pat. No. 5,756,544, 1998.
18. J. Bar-Tana, U. S. Pat. No. 4,689,344, 1987.
19. J. Bar-Tana et al. U. S. Pat. No. 4,711,896, 1987.
20. S. M. Berge et al. *J. Pharmaceutical Sciences* 1977, 66, 1 et seq.
21. Prescott, Ed., *Methods in Cell Biology*, Volume XIV, pp.33 et seq. Academic Press, New York, 1976.

What is claimed is:

1. A dual prodrug compound or a pharmaceutically acceptable salt thereof of Formula 1, Formula 1

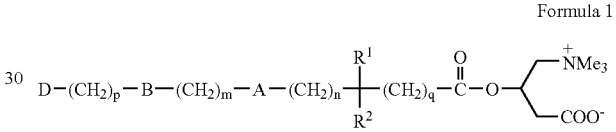

wherein A is a single bond, —O—, or —CH$_2$—; m and n vary from 1 to 15; p and q vary from 0 to 1; B is —CR$^3$R$^4$; D is selected from the group consisting of —CO$_2$R$^5$—OR$^6$, —OCOR$^7$, —SO$_3$R$^8$, —SO$_2$NH$_2$, —OPO(OR$^9$)(OR$^{10}$), —OPO(OR$^9$)(NH$_2$), —OPO(OR$^9$)—O—PO(OR$^{10}$)(OR$^{11}$),

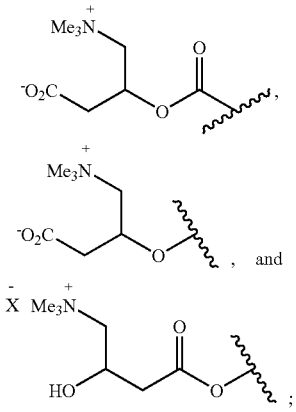

wherein R$^1$ to R$^4$ are independently selected from C$_1$-C$_6$ alkyl; and R$^5$ to R$^{11}$ are independently selected from the group consisting of hydrogen; C$_1$-C$_6$ alkyl; C$_3$-C$_6$ cycloalkyl; C$_2$-C$_6$ alkenyl; C$_6$ alkynyl; C$_5$-C$_{10}$ aryl unsubstituted or substituted with C$_1$-C$_6$ alkyl, hydroxyl, C$_1$-C$_6$ alkoxyl, 1,3-dioxolanyl, cyano, halo, nitro, trihaloalkyl, carboxyl, C$_1$-C$_6$ acyl, C$_1$-C$_6$ hydroxyalkyl, amino, C$_1$-C$_6$ alkylamino, C$_1$-C$_6$ dialkylamino, C$_1$-C$_6$ acylamino, and C$_1$-C$_6$ alkxoylcarbonyl; C$_5$-C$_6$ arylalkyl unsubstituted or substituted with C$_1$-C$_6$ alkyl, hydroxyl, C$_1$-C$_6$ alkoxyl, 1,3-dioxolanyl, cyano, halo, trihaloalkyl, carboxyl, $C_1$-$C_6$ acyl, $C_1$-$C_6$ hydroxyalkyl, amino, $C_1$-$C_6$ alkylamino, $C_1$-$C_6$ dialkylamino, and $C_1$-$C_6$ alkxoylcarbonyl; $C_1$-$C_6$ carboxyalkyl; $C_1$-$C_6$ acylamino; $C_1$-$C_6$ sulfonatoalkyl; $C_1$-$C_6$ sulfamylalkyl; and $C_1$-$C_6$ phosphonatoalkyl.

2. The compound of claim 1, wherein A is a single bond, —O—, or —$CH_2$—; m and n vary from 1 to 6; p and q vary from 0 to 1; B is —$CR^3R^4$; D is selected from the group consisting of —$CO_2R^5$, —$OR^6$, and

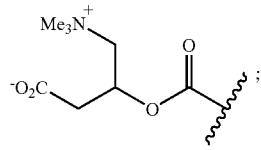

and $R^1$ to $R^4$ are independently selected from the group consisting of $C_1$-$C_6$ alkyl, and $R^5$ and $R^6$ are independently selected from the group consisting of hydrogen, $C_1$-$C_6$ alkyl, and $C_3$-$C_6$ cycloalkyl.

3. The compound of claim 1, wherein A is —O—; m is 4; n is 4; p varies from 0 to 1; q is 0 or 1; B is —$CR^3R^4$; D is selected from the group consisting of —$CO_2R^5$, —$OR^6$, and

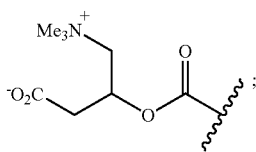

and $R^1$ to $R^4$ are methyl groups; $R^5$ is hydrogen or an ethyl group; and $R^6$ is hydrogen.

4. The compound of claim 1, wherein A is —$CH_2$—; B is —$CR^3R^4$; m is 4; n is 5; p varies from 0 to 1; q is 0 or 1; D is selected from the group consisting of —$CO_2R^5$, —$OR^6$, and

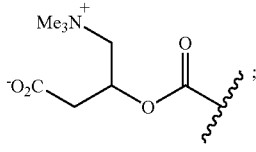

and $R^1$ to $R^4$ are methyl groups; $R^5$ is hydrogen or an ethyl group; and $R^6$ is hydrogen.

* * * * *